United States Patent
Honore et al.

(10) Patent No.: US 10,633,307 B2
(45) Date of Patent: Apr. 28, 2020

(54) METHOD FOR INERTING ACTIVATED CARBON IN BIOGAS PURIFICATION EQUIPMENT

(71) Applicant: Calgon Carbon Corporation, Moon Township, PA (US)

(72) Inventors: Franck Michel Honore, Paris (FR); Thomas Anthony Ryan, Cheshire (GB)

(73) Assignee: CALGON CARBON CORPORATION, Moon Township, PA (US)

( * ) Notice: Subject to any disclaimer, the term of this patent is extended or adjusted under 35 U.S.C. 154(b) by 0 days.

(21) Appl. No.: 15/168,496

(22) Filed: May 31, 2016

(65) Prior Publication Data

US 2016/0346723 A1 Dec. 1, 2016

Related U.S. Application Data

(60) Provisional application No. 62/169,090, filed on Jun. 1, 2015.

(51) Int. Cl.
*C07C 7/12* (2006.01)
*C07C 7/00* (2006.01)
(Continued)

(52) U.S. Cl.
CPC ............ *C07C 7/12* (2013.01); *B01D 53/0407* (2013.01); *C10L 3/104* (2013.01); *B01D 53/86* (2013.01); *B01D 2253/102* (2013.01); *B01D 2256/245* (2013.01); *B01D 2257/304* (2013.01); *B01D 2257/504* (2013.01); *B01D 2257/708* (2013.01); *B01D 2259/402* (2013.01); *B01D 2259/40086* (2013.01); *C10L 3/103* (2013.01); *C10L 2290/10* (2013.01); *C10L 2290/46* (2013.01);
(Continued)

(58) Field of Classification Search
CPC ................ C07C 7/12; C07C 7/00; C07C 7/13
See application file for complete search history.

(56) References Cited

U.S. PATENT DOCUMENTS 4,701,187 A   10/1987   Choe et al.
5,089,034 A *  2/1992   Markovs ................ B01D 53/04
                                                          95/123
(Continued)

FOREIGN PATENT DOCUMENTS

EP   0341879 B1   4/1992
GB   2055609 A    3/1981
(Continued)

OTHER PUBLICATIONS

Florida Power and Light Company, Natural gas spec sheet, 2004, prepared by Florida Power and Light Company.*
(Continued)

*Primary Examiner* — Youngsul Jeong
(74) *Attorney, Agent, or Firm* — Pepper Hamilton LLP

(57) ABSTRACT

Various embodiments of the present invention are directed to methods of preparing a biogas purification system. Embodiments include flushing an adsorber with a gas stream that is separable by the downstream biogas purification process. Other embodiments include using the separable gas stream to flush a saturated adsorber. Additional embodiments include using a gas stream comprised of $CO_2$.

4 Claims, 5 Drawing Sheets

(51) Int. Cl.
*C07C 7/13* (2006.01)
*B01D 53/04* (2006.01)
*C10L 3/10* (2006.01)
*B01D 53/86* (2006.01)

(52) U.S. Cl.
CPC ... *C10L 2290/543* (2013.01); *C10L 2290/548* (2013.01); *Y02C 10/08* (2013.01)

(56) References Cited

U.S. PATENT DOCUMENTS

| | | | |
|---|---|---|---|
| 8,568,512 | B2 | 10/2013 | Siegel et al. |
| 2011/0185896 | A1 | 8/2011 | Sethna et al. |
| 2014/0053724 | A1* | 2/2014 | Raatscher ............ B01D 53/04 95/11 |
| 2015/0119623 | A1 | 4/2015 | Huang |

FOREIGN PATENT DOCUMENTS

| | | |
|---|---|---|
| JP | H01-127021 A | 5/1989 |
| JP | H07505116 A | 6/1995 |
| JP | 2000015053 A | 1/2000 |
| JP | 2008045060 A | 2/2008 |
| JP | 2009249571 A | 10/2009 |
| JP | 2014100655 A | 6/2014 |
| KR | 101444186 B1 | 9/2014 |
| WO | 94/16990 A1 | 8/1994 |
| WO | 2014118262 A1 | 8/2014 |
| WO | WO-2014118262 A1 * | 8/2014 ......... B01D 53/0465 |

OTHER PUBLICATIONS

International Search Report and Written Opinion for PCT/US2016/034964 dated Aug. 23, 2016.
Supplementary European Search Report issued for European Patent Application No. 16804204.2 dated Nov. 23, 2018.

* cited by examiner

US 10,633,307 B2

METHOD FOR INERTING ACTIVATED CARBON IN BIOGAS PURIFICATION EQUIPMENT

CROSS-REFERENCE TO RELATED APPLICATIONS

This application claims priority from U.S. Provisional No. 62/169,090 entitled "Method for Inerting Activated Carbon in Biogas Purification Equipment," filed Jun. 1, 2015, the contents of which are hereby incorporated by reference in their entirety.

GOVERNMENT INTERESTS

Not applicable

PARTIES TO A JOINT RESEARCH AGREEMENT

Not applicable

INCORPORATION BY REFERENCE OF MATERIAL SUBMITTED ON A COMPACT DISC

Not applicable

BACKGROUND

Not applicable

SUMMARY OF THE INVENTION

Various embodiments of the present invention are directed to methods of preparing a biogas purification system. Embodiments include flushing an adsorber with a gas stream that is separable by the downstream biogas purification process. Other embodiments include using the separable gas stream to flush a saturated adsorber. Additional embodiments include using a gas stream comprised of $CO_2$.

DETAILED DESCRIPTION

Figure 1:
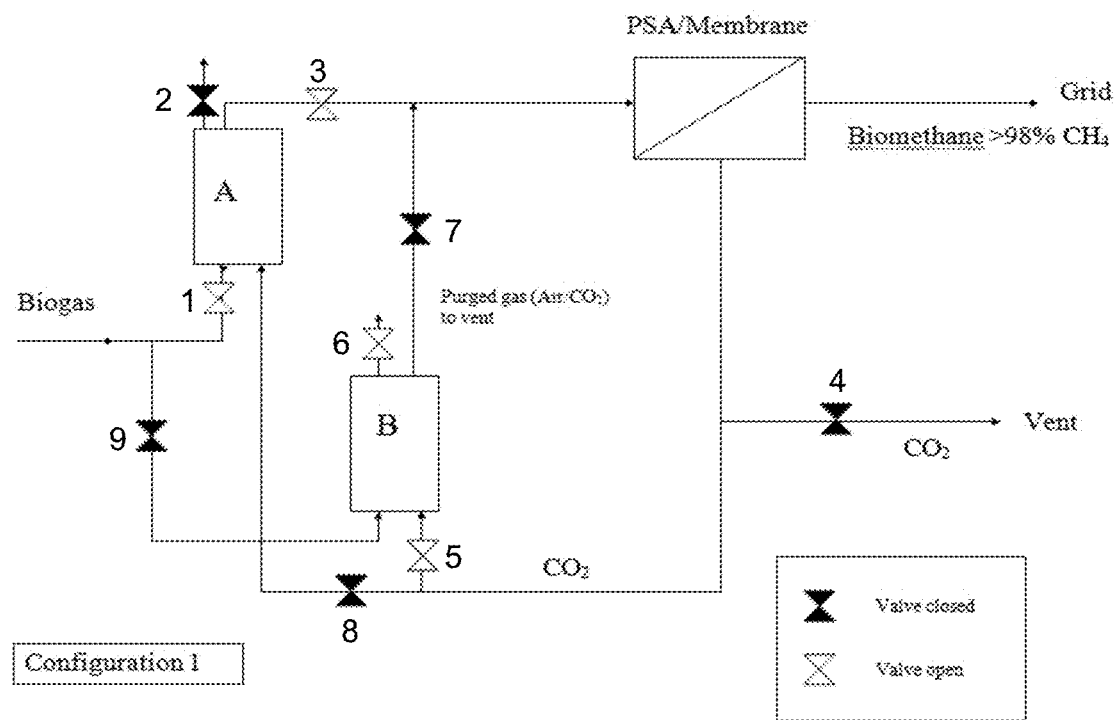
FIG. 1 illustrates an example configuration of the present invention. In this configuration, biogas is admitted to adsorber A for the removal of organics and $H_2S$. The valve to adsorber B remains closed. The effluent stream from adsorber A is passed to a separator for separation of methane and $CO_2$ such as a pressure swing adsorption (PSA). Once it is of sufficient purity, the biomethane can then be admitted to the grid. When the new adsorber, adsorber B, is installed, the $CO_2$ stream can be diverted from the vent to purge adsorber B until all of the air is removed.

This disclosure is not limited to the particular systems, devices and methods described, as these may vary. The terminology used in the description is for the purpose of describing the particular versions or embodiments only, and is not intended to limit the scope.

The following terms shall have, for the purposes of this application, the respective meanings set forth below. Unless otherwise defined, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used in this document, the singular forms "a," "an," and "the" include plural references unless the context clearly dictates otherwise.

"Optional" or "optionally" means that the subsequently described event or circumstance may or may not occur, and that the description includes instances where the event occurs and instances where it does not.

"Biogas" refers to a renewable, environmentally friendly fuel that contributes less to global warming than do traditional fossil fuels. Biogas is produced by the aerobic fermentation of biomass from several sources, including, but not limited to, domestic landfill, manure, raw sewage, sludges, and municipal solid waste.

Raw biogas is comprised mainly of a mixture of methane and carbon dioxide gases, and may have small amounts of nitrogen, hydrogen sulfide, moisture, and siloxanes. The amounts of methane and carbon dioxide components within biogas are variable, and are somewhat dependent upon the organic matter precursor. $CH_4$ concentrations of 50-70 vol. % (mol. %) and $CO_2$ concentrations from 25-38 vol. % (mol. %) are considered typical. When it is purified to fossil natural gas standards, biogas is referred to as "biomethane." For this purification process, carbon dioxide, hydrogen sulfide, water, and other organic contaminants must be removed using one or more methods of separation When the adsorbent media in a biogas purification plant is changed, a large amount of air may be added to the biogas during start-up. The downstream process is not capable of handling a large amount of $N_2$ and $O_2$, the addition of which could downgrade the quality of the resultant biomethane. Consequently, a method is required to reduce the concentration of air in the biogas stream introduced to a separator such as a PSA. Such methods and systems are particularly important when using mobile filters, since the mobile filter is filled remotely from the customer site, where the filter media can then be flushed to remove air that would otherwise be considered a contaminant.

Embodiments of the invention are directed to methods for purifying biogas and purifications systems configured for performing such methods. The methods of such embodiments may include the step of flushing a sorbent with a flushing gas before contacting the sorbent with biogas. Although embodiments are not limited to particular flushing gas, in certain embodiments, the flushing gas may be separable from gasses collected during the purification process by subsequent downstream processing. For example, in some embodiments, the gas may be $CO_2$. The gas used to flush the sorbent may be obtained from an external source or, in particular embodiments, the gas may be obtained by recycling gases from the purification process and using the recycled gas to flush the sorbent. Other embodiments include methods that include the step of flushing spent saturated, or spent, sorbent to purge volatile organic contaminants bound to the sorbent during the purification process. Once flushed, the sorbent is suitable for carbon acceptance and compliant with transport regulations regarding flammable material.

Figure 2:
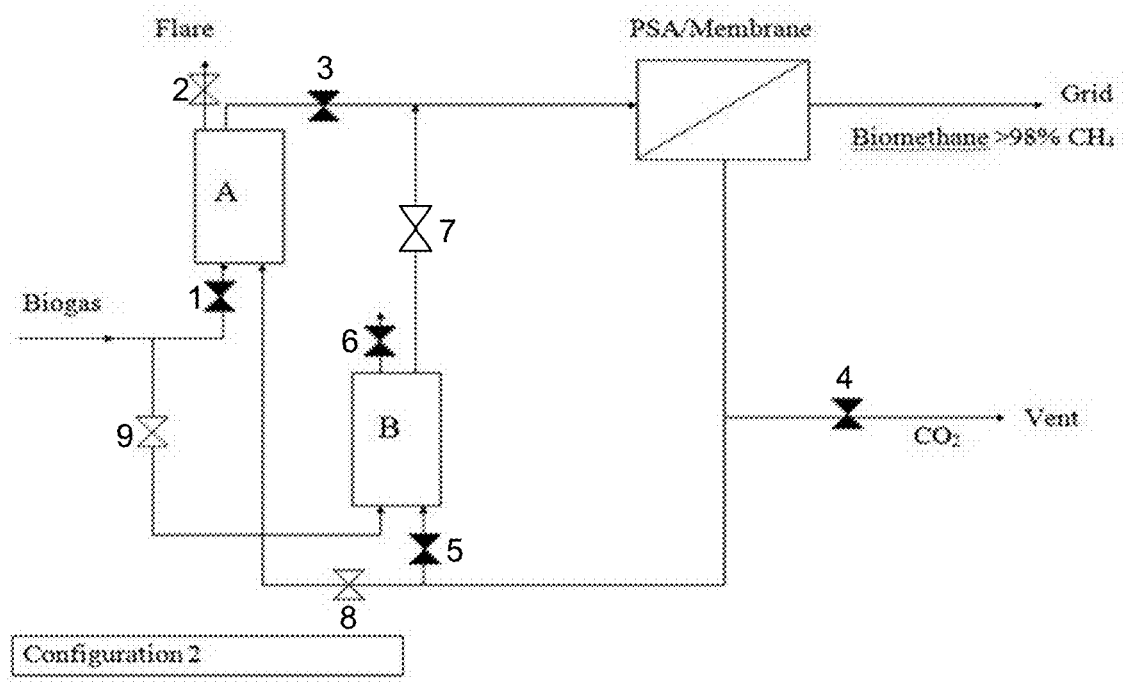
FIG. 2 illustrates an example configuration of the present invention. In this configuration, the valves to adsorber A, which now contains spent carbon, are closed; the biogas stream is diverted to adsorber B, the off-gases from which now pass to a separator such as a PSA unit. The $CO_2$ separated therefrom is passed into adsorber A, and the methane and volatile organics thereby displaced are flared until the flare is naturally extinguished by the entrainment of the $CO_2$ purge gas. Once this is complete, the contents of adsorber A are rendered non-flammable, and the adsorber is ready for removal and transportation, followed by replacement with a new adsorber B.

FIGS. 1 and 2 illustrate an example of a system used to implement the methods described above in which the flushing gas is recycled from a downstream portion of the system that includes two adsorber units containing adsorbent: Adsorber A and Adsorber B. In FIG. 1, biogas enters the system and travels through valve 1 into Adsorber A, where organics and $H_2S$ are removed. The effluent is transported through valve 3 to a separator such as a pressure swing adsorption (PSA) unit where biomethane is separated from carbon dioxide ($CO_2$). The biomethane can be further purified and admitted to the grid. The $CO_2$ removed is typically removed from the system through vent valve 4. In embodiments of the invention, the $CO_2$ can be redirected back through the system to flush Adsorber B, which may contain fresh sorbent, before introducing biogas into Adsorber B. As illustrated in FIG. 1 in some embodiments, $CO_2$ separated at the separator may be routed through valve 5 into Adsorber B and can be purged from the system through purge valve 6. Using two adsorbent vessels (Adsorber A and Adsorber B) allows near-continuous production of the desired purified gaseous stream. It also permits pressure equalization, where the gas leaving the vessel being depressurized is used to partially pressurize the second vessel.

FIG. 2 illustrates the system of FIG. 1 arranged for purification of biogas through Adsorber B. Once the sorbent in Adsorber A is saturated and Adsorber B has been flushed, the biogas stream can be diverted into Adsorber B for removal of organics and $H_2S$ by closing valve 1 and opening valve 9. Organics and $H_2S$ can be removed from the biogas in Adsorber B and the effluent can be passed through valve 7 and into the separator unit where biomethane is separated from $CO_2$. The $CO_2$ can be routed away from Adsorber B and through Adsorber A by closing valve 5 and opening valve 8. The $CO_2$ can be used to purge the volatile organics from Adsorber A through purge valve 2, where the volatile organics can be burned off. After purging, valve 8 can be closed and vent valve 4 can be opened, so the sorbent can be removed from Adsorber A and disposed of. Fresh sorbent can be introduced into Adsorber A, and this sorbent can be flushed by closing vent valve 4 and opening valve 8. The system described in FIGS. 1 and 2, therefore, provides for both flushing and purging of the sorbent, while allowing for continuous flow of biogas through the system.

The sorbent used in Adsorber A and B can be any type of adsorbent known in the art including, but not limited to, carbonaceous char, activated carbon, reactivated carbon, carbon black, graphite, zeolite, silica, silica gel, alumina clay, metal oxides, or a combination thereof. In some embodiments, the sorbent can be a catalyst, or the sorbent can be impregnated with one or more additives that aid in the adsorption of organic impurities and/or hydrogen sulfide.

The catalytic sorbent material may be any sorbent material that can catalyze a reaction known in the art. For example, carbonaceous char is known to enhance a variety of oxidation reactions including, for example, the oxidation of hydrogen sulfide ($H_2S$) and $SO_2$. Such carbonaceous chars act as true catalysts in this capacity because only the rate of a given reaction is affected, and the carbonaceous chars themselves are not changed by the reaction to any significant degree. Thus, in some embodiments, the catalytic adsorbent material may be a carbonaceous char. In other embodiments, the catalytic adsorbent material may be a carbonaceous char that has undergone processing to enhance catalytic activity.

In certain embodiments, the carbonaceous char may be prepared from nitrogen-rich starting materials. Carbonaceous chars prepared from nitrogen-rich starting materials have been shown to catalyze reactions such as hydrogen peroxide decomposition. In other embodiments, the catalytic properties of a carbonaceous char that do not exhibit catalytic activity or that have weak catalytic activity can be enhanced by exposing such chars to nitrogen-containing compounds such as urea, ammonia, polyamide, or polyacrylonitrile. In some embodiments, the exposure of the carbonaceous char to a nitrogen containing compound may be carried out at high temperature such as greater than 700° C. and the carbonaceous char may be heated before, during, or both before and during exposure to the nitrogen containing compound. In other embodiments, exposing the carbonaceous char to a nitrogen containing compound may be carried out at less than 700° C., or low temperature. In still other embodiments, the carbonaceous char may be oxidized at high temperature before being exposed to a nitrogen containing compound.

The carbonaceous char or catalytic activated carbon may be calcined. Calcination may be carried out between any steps in the process. For example, in some embodiments, oxidized carbonaceous char may be calcined before being exposed to a nitrogen containing compound, and in other embodiments, the oxidized carbonaceous char may be calcined after exposure to a nitrogen containing compound or after activation. In still other embodiments, the carbonaceous char may be calcined between more than one step in the process. For example, the carbonaceous char may be calcined after exposure to a nitrogen containing compound and after activation. Calcination is, generally, carried out by heating the carbonaceous char or catalytic activated carbon to a temperature sufficient to reduce the presence of surface oxides on the carbonaceous char. The temperature at which surface oxides are removed may be from about 400° C. to about 1000° C. or any temperature there between, and in some embodiments, the calcination may be carried out in an oxygen-free or otherwise inert environment.

Although embodiments of the invention include any means for separating biomethane from $CO_2$, in some embodiments such as those described in FIG. 1 and FIG. 2, the means for separating biomethane from $CO_2$ may be a pressure swing adsorption (PSA) unit. A PSA unit will typically include a plurality of vessels, each containing a bed of adsorbent material that adsorbs a different gas such as water vapor, $CO_2$, $N_2$, and $O_2$. In some embodiments, the PSA will include vessels containing at least two different adsorbent materials, and in certain embodiments, at least one adsorbent material will be selective for methane, and at least one adsorbent material will be selective for hydrogen. In some embodiments, the adsorbent materials may be positioned in the adsorption vessel in layers. For example, the vessel may include one or more adsorbent material layers selective for methane interspersed with one or more adsorbent material layers selective for hydrogen. Each of the adsorbent materials may be activated carbon, carbon molecular sieves, zeolite, silica gel, alumina clays, and the like and combinations thereof.

The gaseous stream may be passed through the PSA under pressure. The higher the pressure, the more targeted gas component will likely be adsorbed, and when the pressure is reduced, the adsorbed gaseous components can be released, or desorbed. Different target gasses tend to adsorb at different pressures. Therefore, PSA processes can be used to separate one or more gas species from a mixture of gas species by adsorbing and releasing each species at a different pressure. Although PSA is typically operated at near-ambient temperatures, heat can be used to enhance the desorption of adsorbed species. For example, when air passed under pressure through a vessel containing a bed of an adsorbent material that is selective for nitrogen at a pressure that favors nitrogen adsorption, substantially all of the nitrogen will adsorb onto the adsorbent material, and the gaseous stream exiting the vessel will be enriched in oxygen and depleted in nitrogen. When the bed reaches the end of its capacity to adsorb nitrogen, it is regenerated by reducing the pressure, by applying heat, or both releasing the adsorbed nitrogen. It is then ready for another cycle of producing an oxygen enriched stream.

In some embodiments, the biogas processing system may further include a biogas compression system, hydrogen sulfide cleaning system, a moisture knockout vessel, one or more compressors, biogas scrubber system, water supply system, and analysis and final processing system. The various components of the systems of such embodiments may be connected by any suitable means, such as piping, hoses, conduits, and the like and combinations thereof. Such connecting means may conduct the material handled by the particular component of the system between components at the required temperatures and pressures for proper operation. Thus, pressure and temperature may be maintained between components traveling through the connection means. Such systems may further include one or more valves to control the flow of biogas between the components of the system.

In some embodiments, the system may include one or more digesters that remove hydrogen sulfide from the biogas. Such digesters may be positioned upstream or downstream of Adsorbers A and B as illustrated in FIG. 1 and FIG. 2 and may act in concert with Adsorbers A and B to remove hydrogen sulfide. In certain embodiments, digesters may be positioned upstream of adsorbers A and B. Hydrogen sulfide degrades metal equipment and sensors and is therefore typically removed early in the processes and methods described herein. Additionally, hydrogen sulfide is toxic, even when present at very minor concentrations, requiring its removal from the biogas stream.

In particular embodiments, the system may include a moisture separator that reduces the moisture content of the biogas. The moisture separator may be upstream or downstream of Adsorbers A and B, and in certain embodiments, the moisture separator may be upstream of Adsorbers A and B and downstream of the digesters. In some embodiments, the moisture separator may be positioned to remove moisture content present when exiting the digester, and reduce the moisture content to less than about 1.4%. Condensed moisture downstream may create problems for system control, as it interferes with gas flow and pressure measurements. If not removed, condensation can also cause failure of compressor lube oil filters and internal lubricated parts.

The systems of various embodiments may include one or more compressors that pressurize the biogas as it is transported through the system. Compressors may be incorporated at nearly any position in the system. For example, in certain embodiments, a compressor may be incorporated into the system near the start of the system, for example, upstream of the digesters and moisture separator, but downstream of Adsorbers A and B. In other embodiments, compressors may be positioned after Adsorbers A and B, but before a PSA. In still other embodiments, compressors may be positioned both upstream of Adsorbers A and B and downstream of Adsorbers A and B. In further embodiments, a compressor may be positioned after the PSA to pump bio-methane to a storage container, a device configured to operate on bio-methane, or combinations thereof. The compressors of various embodiments may be powered by an electric motor, a biogas-operable motor, or a crude methane-operable motor and the like, and in some embodiments, generators may provide the electricity necessary to power the compressors. Such generators may include biogas-operable motor, or a crude methane-operable motor, and the like. In particular embodiments, the motors may be powered by biogas or methane to allow the systems of embodiments to be self-contained.

In some embodiments, the systems may include an accumulator that combines the biogas streams with recycled gas streams coming from other portions of the system such as a flash tank or gas drier. The combined biogas stream can then be directed from the accumulator into a system upstream of, for example, Adsorbers A and B or the PSA. In other embodiments, the combined biogas may be introduced into the system upstream of the moisture separator.

In certain embodiments, the system may include a cooler which may reduce the temperature of the biogas stream below about 70° F. (about 21° C.). The cooler may be positioned anywhere within the system, and in certain embodiments, the cooler may be positioned immediately upstream of the PSA or a scrubber, which is described below.

Some embodiments of the systems of the invention may include a biogas scrubber. Such scrubbers typically remove carbon dioxide from biogas through water absorption. Carbon dioxide is more soluble in water under pressure than at atmospheric pressure, whereas methane is mostly insoluble in water, even at elevated pressures. Pressurizing a methane/carbon dioxide biogas mixture in the presence of water drives the carbon dioxide into solution in the water, but little methane is dissolved into solution. The gas flows in counter-flow or cross-flow with the water. The resulting processed biogas has an enriched methane content, because some or all of the carbon dioxide has been processed out of the gas and into the water solution. The compressed operating pressure is a function of the temperature, carbon dioxide mole fraction in the gas, and the desired methane purity. Such scrubbers may be located downstream of a cooler, and are typically downstream of Adsorbers A and B and downstream of the PSA. In certain embodiments, the scrubber system may be connected to a water supply system that pumps water into the scrubber system.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples. The following examples are for illustrative purposes only, and are not to be construed as limiting the invention in any manner.

Example 1

The dynamics of oxygen displacement by carbon dioxide flushing through an activated carbon-filled adsorber were studied for engineering design purposes. The number of bed-volumes required to inert a carbon filled column was determined as a function of $CO_2$ gas velocity. Similarly, the inerting of a methane-loaded activated carbon column by $CO_2$ flushing has been studied to determine the degree of purging required for compliance with transportation and safety regulations.

In particular, the laboratory studies were required to provide experimental data for evaluating the effectiveness of a $CO_2$ gas flushing procedure to effect a safe 'inerting' of the activated carbon in service filter equipment used for biogas purification. Biogas is comprised mainly of a mixture of methane and carbon dioxide gases, and may have small amounts of hydrogen sulfide, moisture, and siloxanes. The amounts of methane and carbon dioxide components within biogas are variable, and are somewhat dependent upon the organic matter precursor. $CH_4$ concentrations of 50-70 vol. % (mol. %) and $CO_2$ concentrations from 25-38 vol. % are considered typical.

The laboratory-scale 'inerting' tests were carried out at ambient conditions of temperature and pressure. Tests simulated flushing of a biogas adsorption system (when filled with an activated carbon) by 99.5% $CO_2$ gas. The laboratory 'inerting' studies simulated two separate, different stages of the filter equipment utilization, i.e., (a) oxygen removal from a 'new-filled' adsorption system prior to its 'on-stream' application for biogas purification; and (b) methane removal from a 'used' carbon filter system, to thus 'make-safe' for transportation and de-commissioning operations (i.e., carbon emptying).

The studies used a vertical, cylindrical test-rig (250 mL internal volume) and evaluated various rates of 'down-flow $CO_2$', thus providing data for variations in contact time and gas velocity though the carbon bed. Testing evaluated separate flushing out with $CO_2$ gas of four selected pelletized Chemviron Carbon grades. For comparison purposes, the extruded test carbons comprised two impregnated grades that are generally advocated for biogas purification, and two grades of base carbon pellets (i.e., without impregnation) that represented the precursor pellets for the two impregnated test carbons.

Test carbons included: (i) SOLCARB®KS3, a high performance impregnated 3 mm pelletized product specifically developed for rapid vapor phase removal of hydrogen sulfide, organic mercaptans, and certain organic sulfides; (ii) ENVIROCARB® STIX®, an impregnated extruded carbon (4 mm pellets) designed for the removal of hydrogen sulfide, acid gases and other odorous compounds from air; (iii) ENVIROCARB® AP3-60, an extruded base carbon (3 mm pellets), which represented the precursor base for SOLCARB®KS3 manufacture; and (iv) ENVIROCARB® AP4-50, an extruded base carbon (4 mm pellets), which represented the precursor carbon base for ENVIROCARB® STIX® manufacture.

A rigid plastic tube test-rig was vertically oriented. Tube dimensions are shown below in TABLE 1.

TABLE 1

| | |
|---|---|
| Test-rig tube length | 47 cm |
| Internal diameter | 2.6 cm |
| Calculated cross-sectional area | 5.31 $cm^2$ |
| Calculated internal volume | 249.6 $cm^3$ |

$CO_2$ gas flow (99.5% purity) was obtained from a regulated high-pressure $CO_2$ cylinder. $CO_2$ flow-rate control and measurement was conducted through a rotameter-type flow meter recalibrated for $CO_2$ gas.

The 250 ml test-rig was first filled with a recently obtained sample of pelletized test carbon (no pre-drying), and the weight of test sample was recorded. Under this carbon-filled condition, the test-rig also contained a certain proportion of air/oxygen; present in both the inter-pellet spaces, and also adsorbed in the carbon pore structure. The aim of the inerting was to affect a removal of oxygen from the adsorbent column system to <0.1% by 'flushing out' with a controlled downward flow of 99.5% purity $CO_2$ gas, at ambient conditions of temperature and pressure.

The initial trial used a sample of SOLCARB®KS3 pellets. The weight of sample carbon used to fill the 250 mL test-rig was recorded. A $CO_2$ flow-rate of 2 liters per minute was connected to the top of the carbon filled test-rig column, and a digital timer was started. The 2 liters/minute $CO_2$ gas flow corresponded to a calculated gas velocity of 6.3 cm per second through the test-rig. At intervals during the course of $CO_2$ gas flow and flushing-out, the effluent gas from the bottom of the adsorber was sampled by calibrated syringe, and was analyzed for its oxygen component using the laboratory GC/MS (Agilent 7890A Gas Chromatograph and 5975C Mass Spectrometer) with the appropriate GC column, pre-calibrated for $O_2$ concentration.

Figure 3:
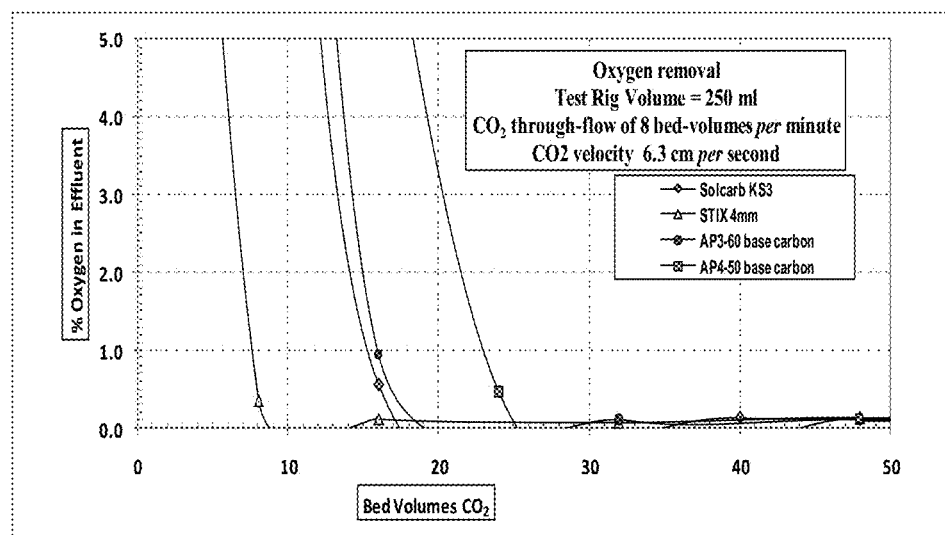
FIG. 3 illustrates oxygen concentration during $CO_2$ purging at a gas velocity of 6.3 cm/second through a 250 mL test-rig.

Due to the 2-minute oxygen residence time in the GC column, sampling of effluent gas from the test column was possible every 2 to 3 minutes. $CO_2$ gas flow was continued through the test adsorbent until the $O_2$ concentration was <0.1%. On completion of the adsorbent test, the flushed out carbon sample was removed from the test-rig, and its 'flushed out' weight was recorded. Samples of the other three test carbons were then similarly tested at a 6.3 cm/second velocity flow of $CO_2$ gas, and the oxygen % results were recorded at several flow times. A summary of the oxygen % test values for the flushing out at 2 liters/minute flow $CO_2$ for the four carbons is shown in TABLE 2 below, and in FIG. 3.

TABLE 2

Four test carbons - $O_2$ concentration during $CO_2$ purging at gas velocity 6.3 cm/second through 250 mL test-rig

| | |
|---|---|
| $CO_2$ flow rate | 2 liters per minute |
| $CO_2$ flow rate | 8 empty bed-volumes per minute |
| $CO_2$ velocity though carbon | 6.3 cm per second |

TABLE 2-continued

Four test carbons - O$_2$ concentration during CO$_2$ purging at gas velocity 6.3 cm/second through 250 mL test-rig

| Solcarb KS3 | | STIX 4 mm | | AP3-60 base | | AP4-50 base | |
|---|---|---|---|---|---|---|---|
| Bed-Volumes | % Oxygen | Bed-Volumes | % Oxygen | Bed-Volumes | % Oxygen | Bed-Volumes | % Oxygen |
| 0 | 20.93 | 0 | 20.93 | 0 | 20.93 | 0 | 20.93 |
| 8 | 15.91 | 8 | 0.35 | 8 | 18.42 | 8 | 18.00 |
| 16 | 0.13 | 16 | 0.12 | 16 | 0.94 | 24 | 0.46 |
| 40 | 0.13 | 32 | 0.07 | 32 | 0.10 | 48 | 0.12 |
| 80 | 0.09 | 48 | 0.13 | 48 | 0.10 | 80 | 0.08 |
| — | — | 80 | 0.12 | 80 | 0.10 | — | — |

Test values at a CO$_2$ velocity of 6.3 cm/second indicated fairly rapid purging of the oxygen from the test rig. For all the test carbons, the % O$_2$ in the effluent was reduced to <0.1% by about 30 to 40 bed-volumes flow (i.e., representing 4 to 5 minutes CO$_2$ flow). The two base carbons appeared to take a slightly longer time for oxygen flushing than the two impregnated grades. For all test samples, there was no discernible 'exotherm' during the CO$_2$ purging.

After scrutiny of the test values obtained with a CO$_2$ purge velocity of 6.3 cm per second, additional purge gas velocities were similarly assessed for the effect on the oxygen reduction. Purge flow rates of 0.5, 1.0 and 6.0 liters CO$_2$ per minute were evaluated.

The ENVIROCARB® AP3-60 base carbon was chosen as the adsorbent for the variable velocity purge testing, and was thought to represent the typical purging properties of the other test carbons. After each purge test, the ENVIROCARB® AP3-60 carbon was discarded and the test-rig refilled with a 'fresh' amount of base carbon. The variable CO$_2$ purge gas conditions tested for the ENVIROCARB® AP3-60 carbon tested are shown in TABLE 3 below.

TABLE 3

Variable Purge Gas conditions for ENVIROCARB ® AP3-60 test carbon

| CO$_2$ purging flow rate Liters per minute | CO$_2$ purging flow rate Bed-Volumes per minute | CO$_2$ purging Velocity cm per second |
|---|---|---|
| 0.5 | 2 | 1.6 |
| 1.0 | 4 | 3.2 |
| 2.0 | 8 | 6.3 |
| 6.0 | 24 | 18.8 |

Figure 4:
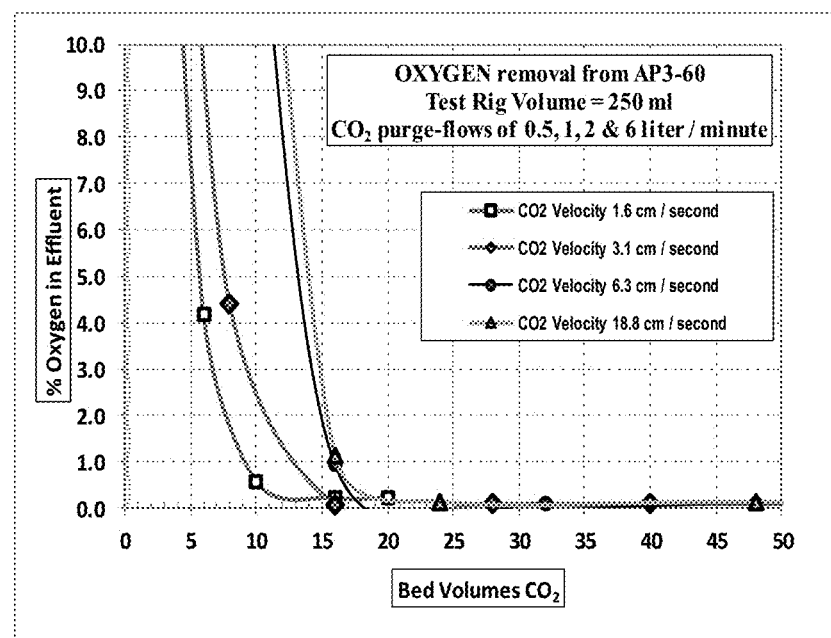
FIG. 4 illustrates oxygen concentration during variable velocities of $CO_2$ purging AP3-60 carbon.

The % O$_2$ test values obtained in the gaseous effluent during the different purge gas velocity conditions are shown in TABLE 4 and FIG. 4.

TABLE 4

AP3-60 carbon - Oxygen removal as a function of variable purge gas conditions

| | Oxygen purging of AP3-60 base carbon | | | |
|---|---|---|---|---|
| CO$_2$ Flow-Rate Litres per minute | 0.5 | 1.0 | 2.0 | 6.0 |
| Bed-volumes per minute | 2 | 4 | 8 | 24 |
| Velocity cm per second | 1.6 | 3.2 | 6.3 | 18.8 |

| Bed-Vols | % O$_2$ | Bed-Vols | % O$_2$ | Bed-Vols | % O$_2$ | Bed-Vols | % O$_2$ |
|---|---|---|---|---|---|---|---|
| 0 | 20.93 | 0 | 20.93 | 0 | 20.93 | 0 | 20.93 |
| 2 | 20.80 | 4 | 16.53 | 8 | 18.42 | 8 | 19.80 |

TABLE 4-continued

AP3-60 carbon - Oxygen removal as a function of variable purge gas conditions

| 6 | 4.17 | 8 | 4.39 | 16 | 0.94 | 16 | 1.14 |
|---|---|---|---|---|---|---|---|
| 10 | 0.59 | 16 | 0.08 | 32 | 0.10 | 24 | 0.14 |
| 16 | 0.23 | — | — | — | — | 48 | 0.13 |
| 20 | 0.22 | — | — | — | — | — | — |

Test values indicated an inverse relationship between CO$_2$ purging velocity and the reduction rate in oxygen concentration. That is, the slower the purging CO$_2$ velocity, the quicker the speed of oxygen removal.

Values indicate that the purging effectiveness was primarily dependent upon adsorption (and diffusion) kinetics within the carbon/air system. (i.e., adsorption of CO$_2$ gas and removal of adsorbed air removal from the carbon pore structure). The initial air removal, and the continuing removal of desorbed air/oxygen from the pore structure into the inter-pellet voids, would be relatively quick.

Notwithstanding the effects of adsorption kinetics, all the CO$_2$ purge velocities tested removed oxygen from the test-rig fairly quickly, and indicated that about 16 to 20 bed-volumes of purging was effective.

Example 2

The aim of this study was to assess the effectiveness of a CO$_2$ purge flow for the safe removal of methane from a 'used' biogas carbon filter system, to thus 'make-safe' before any transportation or de-commissioning operations.

The laboratory 250 mL test rig described above was again employed, together with the two impregnated pelletized carbon grades and their respective base carbon precursors. Prior to a carbon being tested, it was filled into the test-rig and then allowed to saturate and equilibrate in a 1 liter per minute flow of 99.9% methane gas for 30 minutes.

The methane-saturated test carbon was then similarly flushed out with a 1 liter per minute purge flow of CO$_2$ gas. At timed intervals, a sample of the effluent gas was analyzed for % CH$_4$, using the Agilent GC/MS pre-calibrated for methane concentration.

Figure 5:
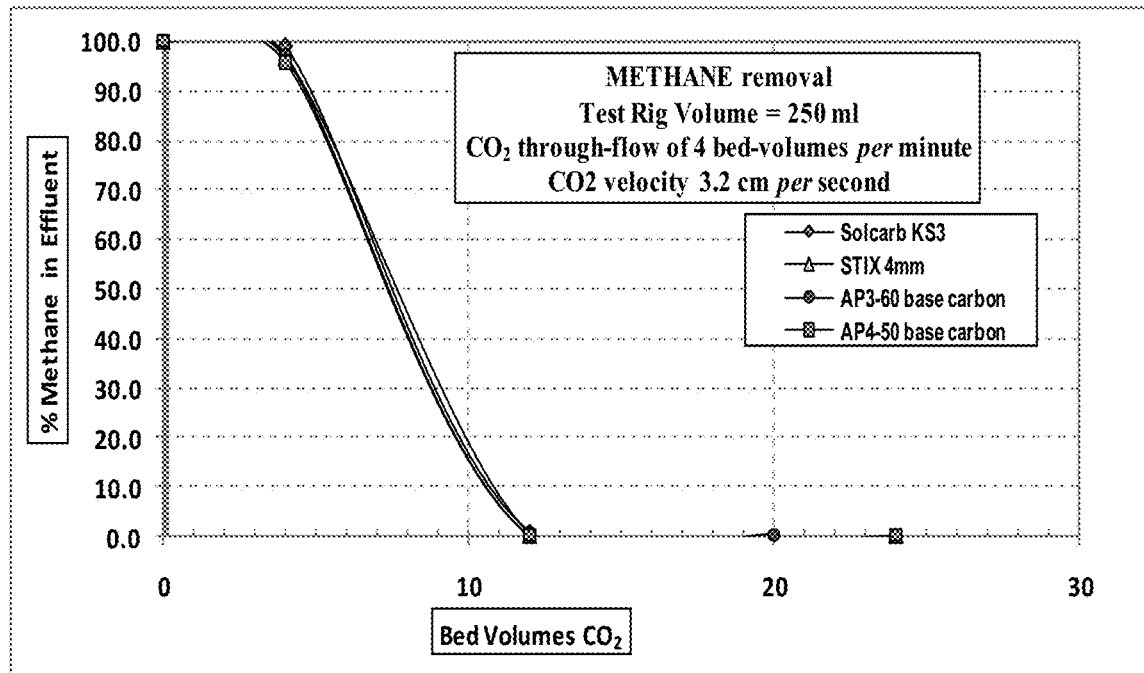
FIG. 5 illustrates methane concentration during $CO_2$ purging at a gas velocity of 3.2 cm/second through a 250 mL test-rig.

A summary of the methane % test values for the flushing out at 1 liter/minute flow CO$_2$ for the four carbons is shown in TABLE 5 and FIG. 5.

TABLE 5

Four test carbons - CH₄ concentration during CO₂ purging at gas velocity 6.3 cm/second through 250 mL test-rig

| CO$_2$ flow-rate | 1 liter per minute |
|---|---|
| CO$_2$ flow-rate | 4 empty bed-volumes per minute |
| CO$_2$ velocity though carbon | 3.2 cm per second |

| Solcarb KS3 | | STIX 4 mm | | AP3-60 base | | AP4-50 base | |
|---|---|---|---|---|---|---|---|
| CO$_2$ Bed-Volumes | % Methane | CO$_2$ Bed-Volumes | % Methane | CO$_2$ Bed-Volumes | % Methane | CO$_2$ Bed-Volumes | % Oxygen |
| 0 | 100 | 0 | 100 | 0 | 100 | 0 | 100 |
| 4 | 98.93 | 4 | 96.71 | 4 | 97.27 | 4 | 95.62 |
| 12 | 1.06 | 12 | 0.15 | 12 | 0.18 | 12 | 0.15 |
| 24 | 0.10 | 24 | 0.15 | 20 | 0.13 | 24 | 0.14 |

Methane gas was readily flushed from all the test carbons by the CO$_2$ purge gas flow. There was very little difference between the four carbon grades tested. Methane concentration in the effluent gas stream was circa 0.1% by about 12 bed-volumes purging with 100% CO$_2$ gas flow. No heat of adsorption was evident during the methane purging tests.

The examples above demonstrate that oxygen removal from the carbon-filled adsorbent vessel, prior to its use for biogas purification, using a 99.5% CO$_2$ purge gas flow was effective.

A slower velocity purge gas flow of CO$_2$ was more effective for oxygen removal from the adsorbent system than was a relatively faster velocity gas purge, due to the kinetics of air desorption rate from the carbon adsorbent.

Methane removal from a 'used' biogas purification vessel (prior to safe de-commissioning and emptying) by flushing with a flow of 99.5% CO$_2$ gas was very rapid and uncomplicated, with no noticeable evolution of heat.

The invention claimed is:

1. A method for purifying a raw biogas, the method comprising:
   providing an adsorber unit containing a sorbent material;
   contacting the sorbent material contained within the adsorber unit with the raw biogas to adsorb organic impurities and/or H$_2$S and thereby form an effluent and a saturated sorbent material, wherein the raw biogas comprises (i) 25-38 vol.% CO$_2$, (ii) methane, and (iii) organic impurities and/or H$_2$S;
   separating CO$_2$ from the effluent, the separated CO$_2$ forming a flushing gas;
   flushing the saturated sorbent material with the flushing gas to produce a flushed sorbent;
   contacting the flushed sorbent with the raw biogas; and
   producing a purified biogas from the effluent.

2. The process of claim 1, wherein the sorbent material is selected from the group consisting of carbonaceous char, activated carbon, reactivated carbon, carbon black, graphite, zeolite, silica, silica gel, alumina clay, metal oxides, and a combination thereof.

3. The process of claim 1, wherein the sorbent material is selected from the group consisting of catalytic adsorbent material, oxidized catalytic adsorbent material, calcined catalytic adsorbent material, oxidized calcined catalytic adsorbent material, and combinations thereof.

4. The method of claim 1, wherein the purified biogas is biomethane.

* * * * *